US008798762B2

(12) United States Patent
Fain et al.

(10) Patent No.: US 8,798,762 B2
(45) Date of Patent: *Aug. 5, 2014

(54) COMMUNICATION DEVICE, COMMUNICATION SYSTEM AND COMMUNICATION IMPLANTABLE MEDICAL DEVICE

(75) Inventors: Eric S. Fain, Sunnyvale, CA (US); Ronald R. Rios, Thousand Oaks, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 328 days.

This patent is subject to a terminal disclaimer.

(21) Appl. No.: 13/149,608

(22) Filed: May 31, 2011

(65) Prior Publication Data
US 2011/0230734 A1    Sep. 22, 2011

Related U.S. Application Data

(62) Division of application No. 11/972,065, filed on Jan. 10, 2008, now Pat. No. 7,974,702.

(51) Int. Cl.
*A61N 1/00* (2006.01)
*A61N 1/372* (2006.01)

(52) U.S. Cl.
CPC .................................. *A61N 1/37211* (2013.01)
USPC .............................................. 607/60; 607/32

(58) Field of Classification Search
USPC ........................................................... 607/60
See application file for complete search history.

(56) References Cited

U.S. PATENT DOCUMENTS

| 2002/0052539 | A1* | 5/2002 | Haller et al. ................. 600/300 |
| 2003/0144711 | A1* | 7/2003 | Pless et al. ..................... 607/60 |
| 2004/0267330 | A1* | 12/2004 | Lee et al. ........................ 607/48 |
| 2005/0115561 | A1* | 6/2005 | Stahmann et al. ....... 128/200.24 |

* cited by examiner

*Primary Examiner* — Luther Behringer
(74) *Attorney, Agent, or Firm* — Steven M. Mitchell

(57) ABSTRACT

A communication device for an implantable medical device may include: an input/output interface configured to communicate with a wireless communication device; a communication interface configured to communicate with a remote system; and a processor configured to perform an analysis of data received from the wireless communication device via the input/output interface and associated with the implantable medical device. The communication device may include a user interface configured to receive data input by a user. A communication system may include a wireless communication device and the aforementioned communication device. A communication method for an implantable medical device may include: providing a communication device that is configured to communicate with a wireless communication device, to communicate with a remote system and to perform an analysis of data; communicating data associated with an implantable medical device from a wireless device to the communication device; and analyzing the received data at the communication device.

14 Claims, 9 Drawing Sheets

COMMUNICATION DEVICE, COMMUNICATION SYSTEM AND COMMUNICATION IMPLANTABLE MEDICAL DEVICE

PRIORITY CLAIM

The present application is a Divisional of, and claims priority to, U.S. patent application Ser. No. 11/972,065, filed Jan. 10, 2008, entitled "Communication Device, Communication System and Communication method for an Implantable Medical Device," now issued as U.S. Pat. No. 7,974,702, all of which is incorporated herein by reference in its entirety.

REFERENCE TO RELATED APPLICATION

This application is related to pending U.S. patent application Ser. No. 11/555,636, filed Nov. 1, 2006, the entirety of which is incorporated herein by reference.

TECHNICAL FIELD

This application relates generally to implantable medical devices and, more specifically, to devices, systems and methods for communicating with an implantable medical device.

BACKGROUND

A conventional implantable cardiac device may be used to treat fast and/or slow arrhythmias with stimulation therapy including cardioversion, defibrillation, and pacing stimulation. Such stimulation may be prescribed when the patient's heart does not function normally due to, for example, a genetic condition.

An implanted device typically includes a telemetry interface that enables an external device to read data from the implanted device and configure the implanted device. For example, the implanted device may log data relating to the cardiac activity of the patient's heart and corrective stimulation that the implanted device applied to the heart. A treating physician may analyze this data to determine whether to modify the patient's treatment. In addition, based on this data or other tests the physician may reconfigure how the device senses cardiac activity and applies stimulation therapy.

Conventionally, the external device communicates with the implanted device or devices via radio frequency ("RF") signals. For example, the external device connects via a lead to a telemetry head that includes an antenna. When the telemetry head is placed near the implanted device (e.g., on the patient's skin), the telemetry head may send signals to and receive signals from a corresponding telemetry circuit in the implanted device. In general, the external device may include a wireless, e.g., RF, communication element capable of communicating with the implanted devices at relative short distances, for example, two to three meters. The implantable cardiac device and/or a separate "sensor device" for monitoring indicators for heart failure exacerbation may be configured to send and receive signals from either the telemetry head or a wireless communication element.

Traditionally, the external device is used in either a clinical setting or in a patient's home. In the latter case, the external device (e.g., a call-in system) may communicate with a remote computer via a telephone line or cellular communications. In this way, an operator at a remote location may read information from the implanted device or program the implanted device.

SUMMARY

There is a need for improved communication with implantable medical devices. Such communication may be to monitor a patient's condition, to monitor performance of the implantable device, and/or to program or otherwise adjust parameters of the implantable device. In particular, monitoring the patient's condition or the performance of the implantable device may be for providing a corrective response or for providing historical data for analysis.

In one embodiment, a communication device for an implantable medical device may be provided. The communication device may comprise an input/output interface configured to communicate with a wireless communication device, a communication interface configured to communicate with a remote system, and a processor configured to perform an analysis of data received from the wireless communication device via the input/output interface and associated with the implantable medical device.

Alternatively or additionally, some embodiments may comprise a user interface configured to receive data input by a user. In such embodiments, the communication device may include a processor configured to communicate data received from a wireless communication device and data received from the user interface to a remote system.

In one embodiment, a communication system for an implantable medical device may be provided. The communication system may comprise a wireless communication device in conjunction with the aforementioned communication device.

In one embodiment, a communication method for an implantable medical device may be provided. The method may comprise: providing a communication device that is configured to communicate with a wireless communication device, to communicate with a remote system and to perform an analysis of data; communicating data associated with an implantable medical device from a wireless device to the communication device; and analyzing the received data at the communication device.

Alternatively or additionally, some embodiments may comprise: receiving data input by a user via a user interface of the communication device; and communicating data received from the wireless communication device and data received from the user interface to the remote system. In such embodiments, the method may further comprise providing an output to the user based on a result of the analysis via the user interface. Other embodiments may comprise receiving data from an implanted sensor device, processing the received data with the wireless communication device and sending a signal from the wireless communication device that is configured to adjust the cardiac device.

BRIEF DESCRIPTION OF THE DRAWINGS

These and other features, aspects and advantages will be more fully understood when considered with respect to the following detailed description, appended claims and accompanying drawings, wherein:

DETAILED DESCRIPTION

Figure 1:
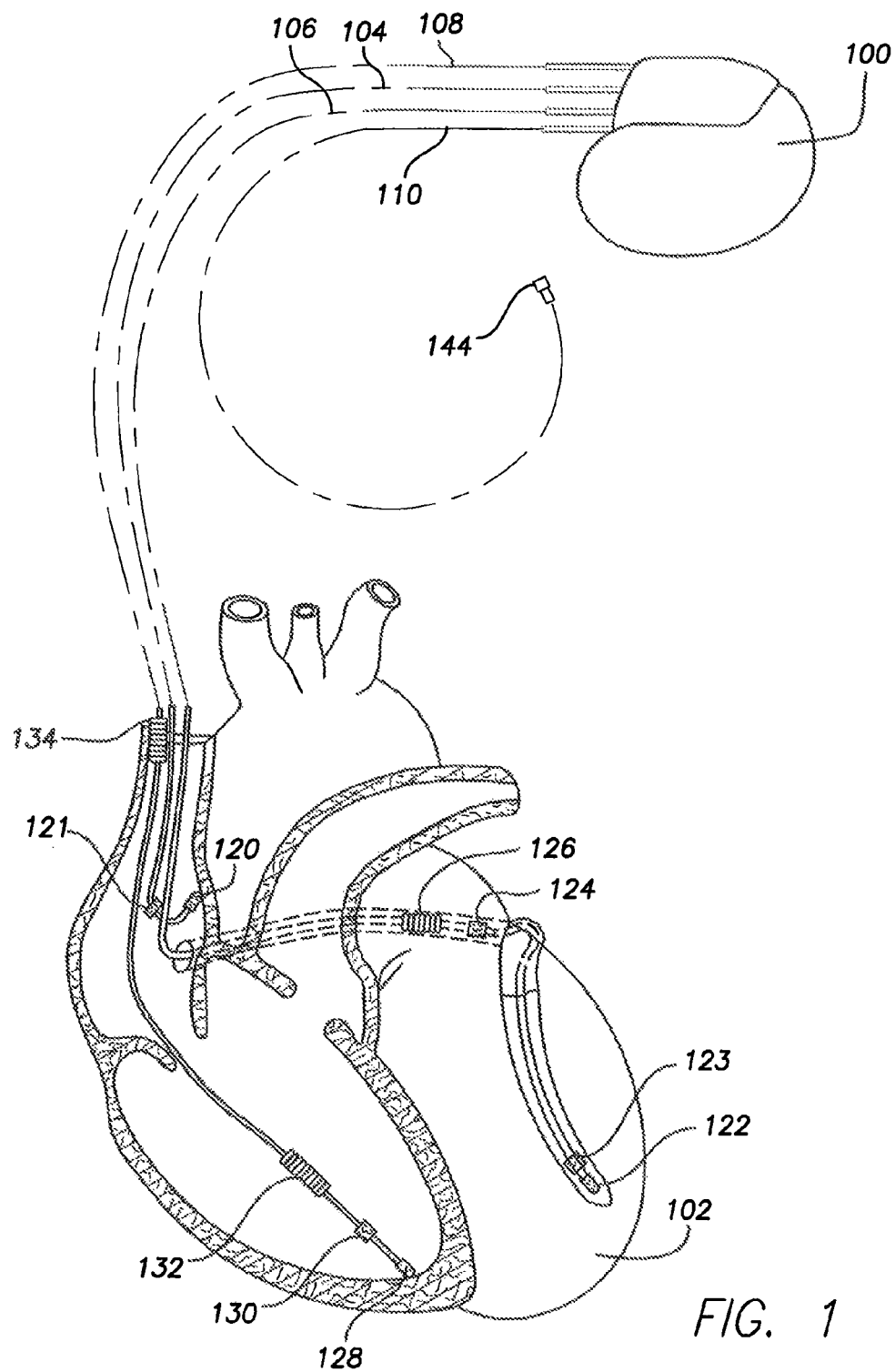
FIG. 1 is a simplified diagram of an example of an implantable stimulation device in electrical communication with at least three leads implanted in a patient's heart for delivering multi-chamber stimulation and shock therapy.

Various details are described below, with reference to illustrative embodiments. It will be apparent that the invention may be embodied in a wide variety of forms, some of which may be quite different from those of the disclosed embodiments. Consequently, the specific structural and/or functional details disclosed herein are merely representative and do not limit the scope of the invention.

For example, based on the teachings herein it should be understood that the various structural and/or functional details disclosed herein may be incorporated in an embodiment independently of any other structural and/or functional details. Thus, an apparatus may be implemented and/or a method practiced using any number of the structural and/or functional details set forth in the disclosed embodiments. Also, an apparatus may be implemented and/or a method practiced using other structural and/or functional details in addition to or other than the structural and/or functional details set forth in the disclosed embodiments.

Embodiments may provide a communication device, system and/or method that provide improved communication with an implantable medical device, such as an implantable cardiac device. For example, a communication device may be configured to receive data from an implantable medical device via a wireless communication device, analyze the received data, and send data to the implantable medical device via the wireless communication device based on the analysis. The communication device may be configured to send data to a remote system based on the analysis. This may allow the communication device to perform some analysis to provide a relatively quick response to the implantable medical device, the user and/or the remote system. Alternatively or additionally, the communication device may read or receive data from one or more implanted sensor devices contained in the patient, perform analysis on the data, and then communicate to the implanted cardiac device based on the data analysis.

Improved communication may also be provided by a communication device that is configured to receive data from an implantable medical device via a wireless communication device and to send the received data to a remote system. In such embodiments, this capability may provide a backup or redundant mode for sending data to the remote system in addition to the capability of the wireless communication device. In particular, such a redundant or backup mode may provide non-wireless communication with the remote system.

Additionally or alternatively, the communication device may be configured to receive data from the implantable medical device and from a user via a user interface of the communication device. This may allow the user to provide additional data for the communication device to analyze and/or to send to a remote system. The user interface may also be configured to provide an output to the user, for example, based on an analysis of the data from the implantable medical device.

Communication provided to the implantable medical device from the communication device via the wireless communication device may program or otherwise adjust operating parameters of the implantable medical device. Such programming or adjustment may be based on analysis of data received by the communication device, the analysis being performed by the communication device and/or a remote system. Alternatively or additionally, the one or more implantable sensor device(s) may receive programming and/or calibration adjustment data based on analysis performed by the wireless device.

Additionally or alternatively, communication provided to the wireless communication device from the communication device may program and/or provide operating or application software to the wireless communication device. Such programming and/or software may provide additional or updated capabilities to the wireless communication device, for example, for interacting with the implantable medical device, the communication device and/or a remote system.

The following description sets forth one example of an implantable cardiac device (e.g., a stimulation device) that is capable of being used in connection with the various embodiments that are described below. It should be understood that other implantable medical devices may be used and that the description below is given to assist in understanding the embodiments described herein.

FIG. 1 shows an exemplary implantable cardiac device 100 in electrical communication with a patient's heart 102 via three leads 104, 106, and 108, suitable for delivering multi-chamber stimulation and shock therapy. To sense atrial cardiac signals and to provide right atrial chamber stimulation therapy, device 100 may be coupled to an implantable right atrial lead 104 including, for example, an atrial tip electrode 120, which typically is implanted in the patient's right atrial appendage or septum, FIG. 1 shows the right atrial lead 104 as including an optional atrial ring electrode 121.

To sense left atrial and ventricular cardiac signals and to provide left chamber pacing therapy, the device 100 may be coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 may be designed to receive atrial and ventricular cardiac signals and to deliver left ventricular pacing therapy using, for example, a left ventricular tip electrode 122 and, optionally, a left ventricular ring electrode 123; to provide left atrial pacing therapy using, for example, a left atrial ring electrode 124; and to provide shocking therapy using, for example, a left atrial coil electrode 126 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference in its entirety.

The device 100 is also shown in electrical communication with the patient's heart 102 via an implantable right ventricular lead 108 including, in this implementation, a right ventricular tip electrode 128, a right ventricular ring electrode 130, a right ventricular (RV) coil electrode 132 (or other electrode capable of delivering a shock), and superior vena cava (SVC) coil electrode 134 (or other electrode capable of delivering a shock). Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 may be capable of sensing or receiving cardiac signals, and delivering stimulation in the form of pacing and shock therapy to the right ventricle.

The device 100 is also shown in electrical communication with a lead 110 including one or more components 144 such as a physiologic sensor. The lead 110 may be positioned in, near or remote from the heart.

It should be understood that the device 100 may connect to leads other than those specifically shown. In addition, the leads connected to the device 100 may include components other than those specifically shown. For example, a lead may include other types of electrodes, sensors or devices that serve to otherwise interact with a patient or the surroundings.

Figure 2:
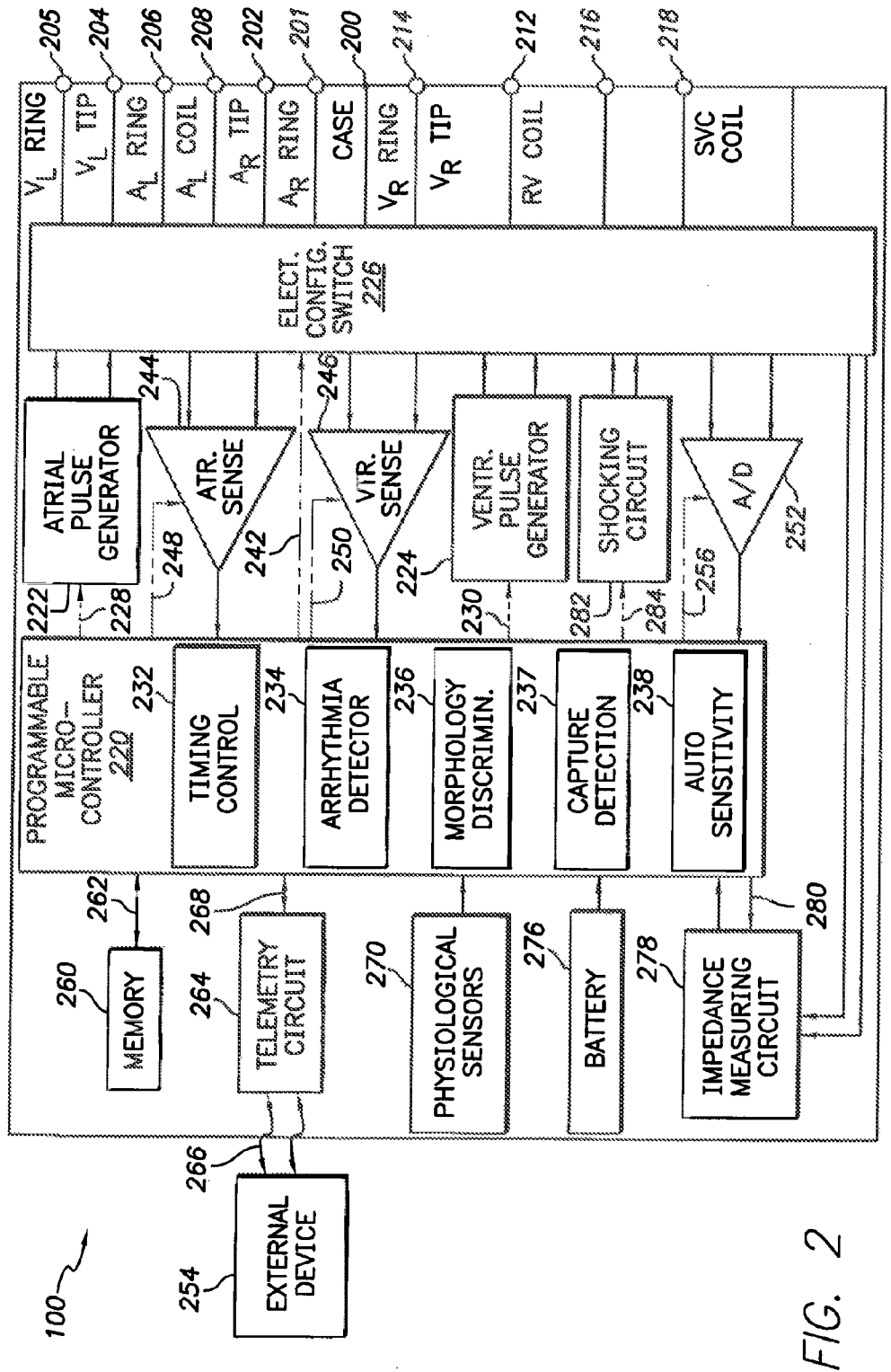
FIG. 2 is a simplified functional block diagram of an example of a multi-chamber implantable stimulation device, illustrating basic elements that are configured to provide cardioversion, defibrillation or pacing stimulation or any combination thereof.

FIG. 2 shows an exemplary, simplified block diagram depicting various components of the cardiac device 100. The device 100 may be capable of treating both fast and slow arrhythmias with stimulation therapy, including cardioversion, defibrillation, and/or pacing stimulation. While a particular multi-chamber device is shown, it should be understood that this is for illustration purposes only. Thus, it should be understood that the approaches described herein may be implemented in connection with any suitably configured or configurable device. Accordingly, the circuitry shown may be duplicated, eliminated, or disabled in any desired combination to provide a device capable of treating the appropriate chamber(s) with, for example, cardioversion, defibrillation, and/or pacing stimulation.

A housing 200 for the device 100 is often referred to as the "can", "case" or "case electrode", and may be programmably selected to act as a return electrode for all "unipolar" modes. The housing 200 may further be used as a return electrode alone or in combination with one or more of the coil electrodes 126, 132 and 134 for shocking purposes. The housing 200 may further include a connector (not shown) including a plurality of terminals 201, 202, 204, 205, 206, 208, 212, 214, 216 and 218 (shown schematically and, for convenience, the names of the electrodes to which they are connected are shown next to the terminals). The connector may be configured to include various other terminals depending on the requirements of the device.

To achieve right atrial sensing and pacing, the connector may include, for example, a right atrial tip terminal (AR TIP) 202 adapted for connection to the atrial tip electrode 120. A right atrial ring terminal (AR RING) 201 may also be included adapted for connection to the atrial ring electrode 121. To achieve left chamber sensing, pacing, and shocking, the connector may include, for example, a left ventricular tip terminal (VL TIP) 204, left ventricular ring terminal (VL RING) 205, a left atrial ring terminal (AL RING) 206, and a left atrial shocking terminal (AL COIL) 208, which may be adapted for connection to the left ventricular tip electrode 122, left ventricular ring electrode 123, the left atrial ring electrode 124, and the left atrial coil electrode 126, respectively.

To support right chamber sensing, pacing, and shocking, the connector may further include a right ventricular tip terminal (VR TIP) 212, a right ventricular ring terminal (VR RING) 214, a right ventricular shocking terminal (RV COIL) 216, and a superior vena cava shocking terminal (SVC COIL) 218, which may be adapted for connection to the right ventricular tip electrode 128, right ventricular ring electrode 130, the RV coil electrode 132, and the SVC coil electrode 134, respectively.

At the core of the device 100 may be a programmable microcontroller 220 that controls the various modes of stimulation therapy. As is well known in the art, the microcontroller 220 typically may include a microprocessor, or equivalent control circuitry, designed specifically for controlling the delivery of stimulation therapy, and may further include memory such as RAM, ROM and/or flash memory, logic and timing circuitry, state machine circuitry, and I/O circuitry. Typically, the microcontroller 220 may include the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments may include the microprocessor-based control system of U.S. Pat. No. 4,940,052 (Mann at al.), the state-machine of U.S. Pat. No. 4,712,555 (Thornander et al.) and U.S. Pat. No. 4,944,298 (Sholder), all of which are incorporated by reference herein in their entirety. For a more detailed description of the various timing intervals that may be used within the device and their inter-relationship, see U.S. Pat. No. 4,788,980 (Mann et al.), also incorporated herein by reference in its entirety.

FIG. 2 also shows an atrial pulse generator 222 and a ventricular pulse generator 224 that may generate pacing stimulation pulses for delivery by the right atrial lead 104, the coronary sinus lead 106, and/or the right ventricular lead 108 via an electrode configuration switch 226. It should be understood that to provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 may be controlled by the microcontroller 220 via appropriate control signals 228 and 230, respectively, to trigger or inhibit the stimulation pulses.

The microcontroller 220 may further include timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The microcontroller 220 may further include an arrhythmia detector 234. The detector 234 may be utilized by the device 100 for determining desirable times to administer various therapies. The detector 234 may be implemented in hardware as part of the microcontroller 220, or as software/ firmware instructions programmed into the device and executed on the microcontroller 220 during certain modes of operation.

The microcontroller 220 may include a morphology discrimination module 236, a capture detection module 237 and an auto-sensing module 238. These modules may optionally be used to implement various exemplary recognition algorithms and/or methods. The aforementioned components may be implemented in hardware as part of the microcontroller 220, or as software/firmware instructions programmed into the device and executed on the microcontroller 220 during certain modes of operation.

The electrode configuration switch 226 may include a plurality of switches for connecting the desired terminals (e.g., that are connected to electrodes, coils, sensors, etc.) to the appropriate I/O circuits, thereby providing complete terminal and, hence, electrode programmability. Accordingly, switch 226, in response to a control signal 242 from the microcontroller 220, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 244 and ventricular sensing circuits (VTR. SENSE) 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial and ventricular sensing circuits, 244 and 246, may include dedicated sense amplifiers, multiplexed amplifiers, or shared amplifiers. The switch 226 may determine the "sensing polarity" of the cardiac signal by selectively closing the appropriate switches, as is also known in the art. In this way, a clinician may program the sensing polarity independent of the stimulation polarity. The sensing circuits (e.g., circuits 244 and 246) may optionally be capable of obtaining information indicative of tissue capture.

Each sensing circuit 244 and 246 may preferably employ one or more low power, precision amplifiers with programmable gain and/or automatic gain control, bandpass filtering, and a threshold detection circuit, as known in the art, to selectively sense the cardiac signal of interest. The automatic gain control may enable the device 100 to deal effectively with the difficult problem of sensing the low amplitude signal characteristics of atrial or ventricular fibrillation.

The outputs of the atrial and ventricular sensing circuits 244 and 246 may be connected to the microcontroller 220, which, in turn, may be able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 may also be capable of analyzing information output from the sensing circuits 244 and 246 and/or the data acquisition system 252. This information may be used to determine or detect whether and to what degree tissue capture has occurred and to program a pulse, or pulses, in response to such determinations. The sensing circuits 244 and 246, in turn, may receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits 244 and 246 as is known in the art.

For arrhythmia detection, the device 100 may utilize the atrial and ventricular sensing circuits 244 and 246 to sense cardiac signals to determine whether a rhythm is physiologic or pathologic. It should be understood that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation which are sometimes referred to as "F-waves" or "Fib-waves") may be classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 252. The data acquisition system 252 may be configured (e.g., via signal line 256) to acquire intracardiac electrogram ("IEGM") signals or other signals, convert the raw analog data into a digital signal, and store the digital signals for later processing and/or telemetric transmission to an external device 254. The data acquisition system 252 may be coupled to the right atrial lead 104, the coronary sinus lead 106, the right ventricular lead 108 and other leads through the switch 226 to sample cardiac signals across any pair of desired electrodes.

The data acquisition system 252 also may be coupled to receive signals from other input devices. For example, the data acquisition system 252 may sample signals from a physiologic sensor 270 or other components shown in FIG. 2 (connections not shown).

The microcontroller 220 may further be coupled to a memory 260 by a suitable data/address bus 262, wherein the programmable operating parameters used by the microcontroller 220 are stored and modified, as required, to customize the operation of the device 100 to suit the needs of a particular patient. Such operating parameters may define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments may be the ability to sense and store a relatively large amount of data (e.g., from the data acquisition system 252), which data may then be used for subsequent analysis to guide programming of the device.

Advantageously, the operating parameters of the implantable device 100 may be non-invasively programmed into the memory 260 through a telemetry circuit 264 in telemetric communication via a communication link 266, either wired or wireless, with an external device 254, such as a programmer, transtelephonic transceiver, or a diagnostic system analyzer. The microcontroller 220 may activate the telemetry circuit 264 with a control signal 268. The telemetry circuit 264 may advantageously allow intracardiac electrograms and status information relating to the operation of the device 100 (as contained in the microcontroller 220 or memory 260) to be sent to the external device 254 through an established communication link 266.

The device 100 may further include one or more physiologic sensors 270. In some embodiments, the device may include a "rate-responsive" sensor that may provide, for example, information to aid in adjustment of pacing stimulation rate according to the exercise state of the patient. One or more physiologic sensors 270 (e.g., a pressure sensor) may further be used to detect changes in cardiac output, changes in the physiological condition of the heart, or diurnal changes in activity (e.g., detecting sleep and wake states). Accordingly, the microcontroller 220 may respond by adjusting the various pacing parameters (such as rate, AV Delay, V-V Delay, etc.) at which the atrial and ventricular pulse generators 222 and 224 generate stimulation pulses.

While shown as being included within the device 100, it should be understood that a physiologic sensor 270 may also be external to the device 100, yet still be implanted within or carried by the patient. Examples of physiologic sensors that may be implemented in conjunction with device 100 include sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference in its entirety.

The one or more physiologic sensors 270 may optionally include sensors to help detect movement (via, e.g., a position sensor) and/or minute ventilation (via an MV sensor) in the patient. Signals generated by the position sensor and MV sensor may be passed to the microcontroller 220 for analysis in determining whether to adjust the pacing rate, etc. The microcontroller 220 may thus monitor the signals for indications of the patient's position and activity status, such as whether the patient is climbing up stairs or descending down stairs or whether the patient is sitting up after lying down.

The device additionally may include a battery 276 that provides operating power to all of the circuits shown in FIG. 2. If the device 100 employs shocking therapy, the battery 276 may be capable of operating at low current drains (e.g., preferably less than 10 μA) for long periods of time, and may be capable of providing high-current pulses (for capacitor charging) when the patient requires a shock pulse (e.g., preferably, in excess of 2 A, at voltages above 200 V, for periods of 10 seconds or more). The battery 276 also may desirably include a predictable discharge characteristic so that elective replacement time may be detected. Accordingly, the device 100 may preferably employ lithium or similar battery technology.

The device 100 may further include magnet detection circuitry (not shown), coupled to the microcontroller 220, to detect when a magnet is placed over the device 100. A magnet may be used by a clinician to perform various test functions of the device 100 and/or to signal the microcontroller 220 that the external device 254 is in place to receive data from or transmit data to the microcontroller 220 through the telemetry circuit 264.

The device 100 may further include an impedance measuring circuit 278 that may be enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 may advantageously be coupled to the switch 226 so that any desired electrode may be used.

In the case in which the device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 may further control a shocking circuit 282 via a control signal 284. The shocking circuit 282 may generate shocking pulses of low (e.g., up to 0.5 J), moderate (e.g., 0.5 J to 10 J), or high energy (e.g., 11 J to 40 J), as controlled by the microcontroller 220. Such shocking pulses may be applied to the patient's heart 102 through, for example, two shocking electrodes, and as shown in this embodiment, selected from the left atrial coil electrode 126, the RV coil electrode 132, and/or the SVC coil electrode 134. As noted above, the housing 200 may act as an active electrode in combination with the RV coil electrode 132, and/or as part of a split electrical vector using the SVC coil electrode 134 or the left atrial coil electrode 126 (i.e., using the RV electrode as a common electrode).

Cardioversion level shocks may generally be considered to be of low to moderate energy level (so as to minimize pain felt by the patient), and/or synchronized with an R-wave and/or pertaining to the treatment of tachycardia. Defibrillation shocks may generally be of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 may be capable of controlling the synchronous or asynchronous delivery of the shocking pulses.

Figure 3:
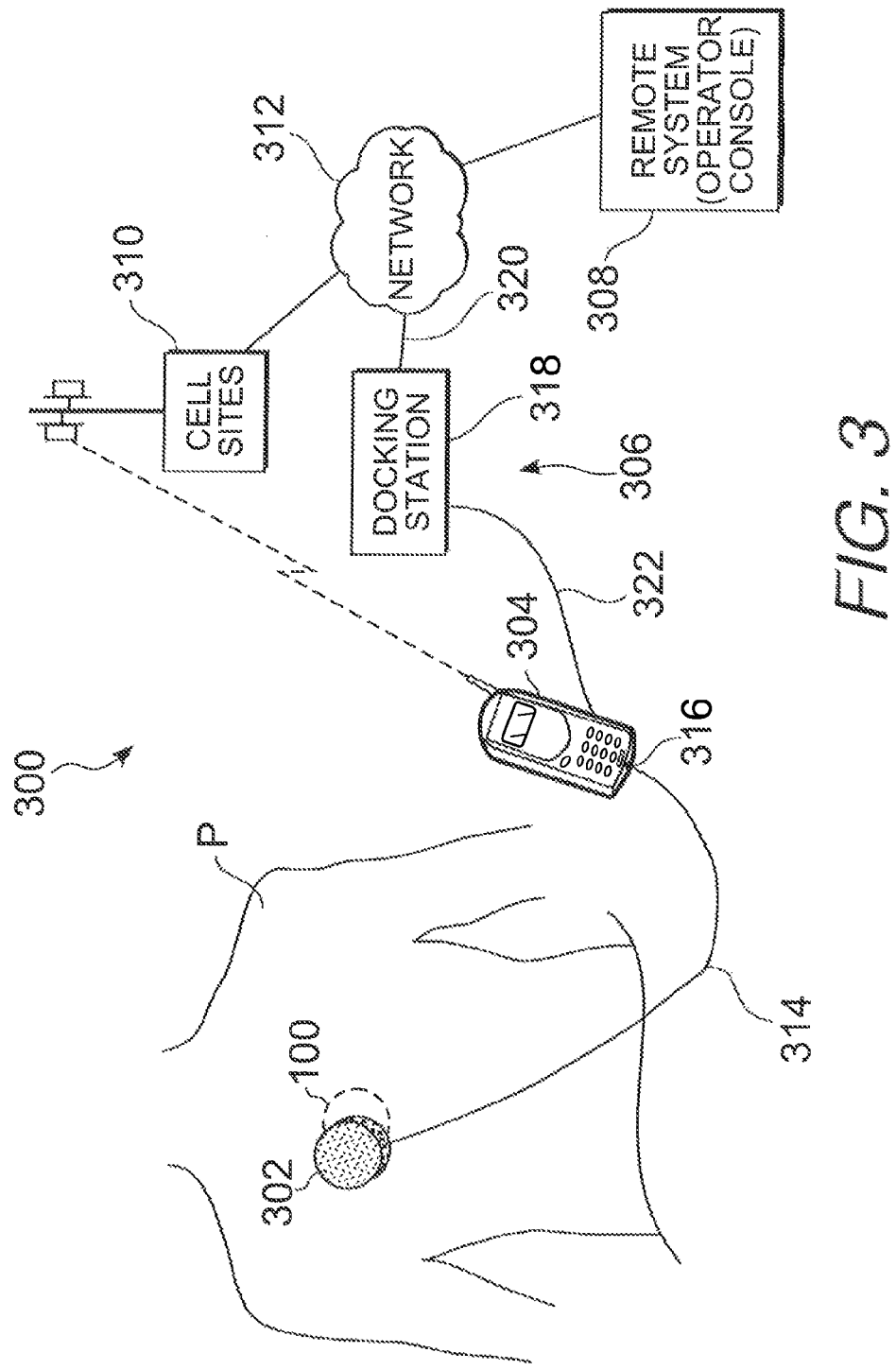
FIG. 3 is a simplified diagram of one embodiment of a communication system.

FIG. 3 illustrates one embodiment of a communication system 300 for an implantable cardiac device 100 implanted in a patient P. The communication system 300 may include a telemetry head 302, a wireless communication device 304, such as a cellular telephone, and a network 312 that facilitate sending data between the implantable cardiac device 100 and a remote system 308. The remote system 308 may include an operator console from which an operator may initiate or assist with the transfer of data between the implantable cardiac device 100 and the remote system 308. In some embodiments the remote system 308 may consist of or include a central server. In this case, a physician may access the central server to send data to or receive data from the implantable cardiac device 100. Further, the remote system 308 may include a capability of analyzing data received from the implantable cardiac device 100.

The communication system 300 may also include a communication device 318, such as a docking station, that is configured to communicate with the wireless communication device 304 and the network 312. A communication link 320 between the communication device 318 and the network 312 may provide non-wireless communication, for example. For example, the communication link 320 may be a hardwired link, such as a telephone line connected to a public switched telephone network (PSTN). It should be understood that the docking station may, additionally or alternatively, include a wireless communication device. A communication link 322 between the communication device 318 and the wireless communication device 304 may provide non-wireless communication, such as a connector or interface, or short-range wireless communication, such as radio frequency (RF).

In accordance with conventional practice, the cellular telephone 304 may communicate with one or more cell sites 310 in a cellular network, which in turn may connect to the network 312 (e.g., the public telephone network, the Internet, etc). The remote system 308 may also be connected, for example, via the network 312. Accordingly, the cellular telephone 304, the communication device 318 and/or the remote system 308 may establish a connection (e.g., a call, a data connection, etc.) to send or receive data via one or more networks.

The telemetry circuit 262 in the implantable cardiac device 100 (FIG. 2) may send telemetry signals to and/or receives telemetry signals from the telemetry head 302 (typically referred to as a "wand"). In some embodiments the telemetry signals comprise RF signals. Other embodiments may incorporate other types of telemetry signals. In embodiments, the telemetry head 302 may be incorporated into the wireless communication device 304, for example, as an integrated device or as software that provides such functionality. It should be understood that the telemetry head 302 may not comprise a "wand," but may provide wireless (e.g., RF) communication and may operate with or without patient interaction.

The telemetry head 302 may be placed relatively close to the device 100 when data is to be downloaded to or uploaded from the implantable cardiac device 100. For example, the implantable cardiac device 100 may be implanted in the upper chest area of the patient (a subcutaneous pectoral implant). Accordingly, the telemetry head 302 may be placed on or just above the patient's skin or clothing in this area.

In embodiments, however, such as those in which the telemetry head 302 is incorporated into the wireless communication device 304, the proximity of the wireless communication device 304 to the patient may be sufficient to provide wireless communication between the implantable cardiac device 100 and the wireless communication device 304. For example, the implantable cardiac device 100 and the wireless communication device 304 may be configured for short-range wireless communication such that normal use of the wireless communication device 304 may maintain a sufficiently close proximity, e.g., the patient carrying the wireless communication device 304, by hand, by purse, by belt, etc., may be within the short range of communication.

Where appropriate or desired, the short range may be expanded to include a room or building, such that communication may be established if the patient sets the wireless communication device 304 down. Especially in such circumstances, it may be useful to provide a secured communication protocol to establish communication only between the implantable cardiac device 100 and the wireless communication device 304, as opposed to another device, such as another implantable cardiac device, that may be within range. Such technology is well known, for example, in related fields such as wireless heartrate monitors.

The telemetry head 302 may communicate with the cellular telephone 304 via a communication link 314. In some embodiments the communication link 314 includes a wired connection mechanism such as one or more signal leads. In this case, the telemetry head 302 may include a lead with a connector 316 that connects to a corresponding connector on the cellular telephone 304. In some embodiments, the communication link 314 includes a wireless connection mechanism using RF, optical or other type of signal. Here, both the telemetry head 302 and the cellular telephone 304 may include a wireless transceiver (not shown in FIG. 3).

In embodiments in which the telemetry head 302, or its equivalent, is incorporated into the wireless communication device 304, the communication link 314 may be internal wiring. It should be appreciated that such embodiments may provide an advantage of convenience for the patient, avoiding a need for the patient to carry, wear and/or properly position a separate component (the telemetry head 302). As a wireless communication device such as a cellular phone is commonly kept close at hand by a majority of individuals in developed countries, the patient is likely to experience little inconvenience to incorporate the communication system 300 into his lifestyle.

Figure 4:
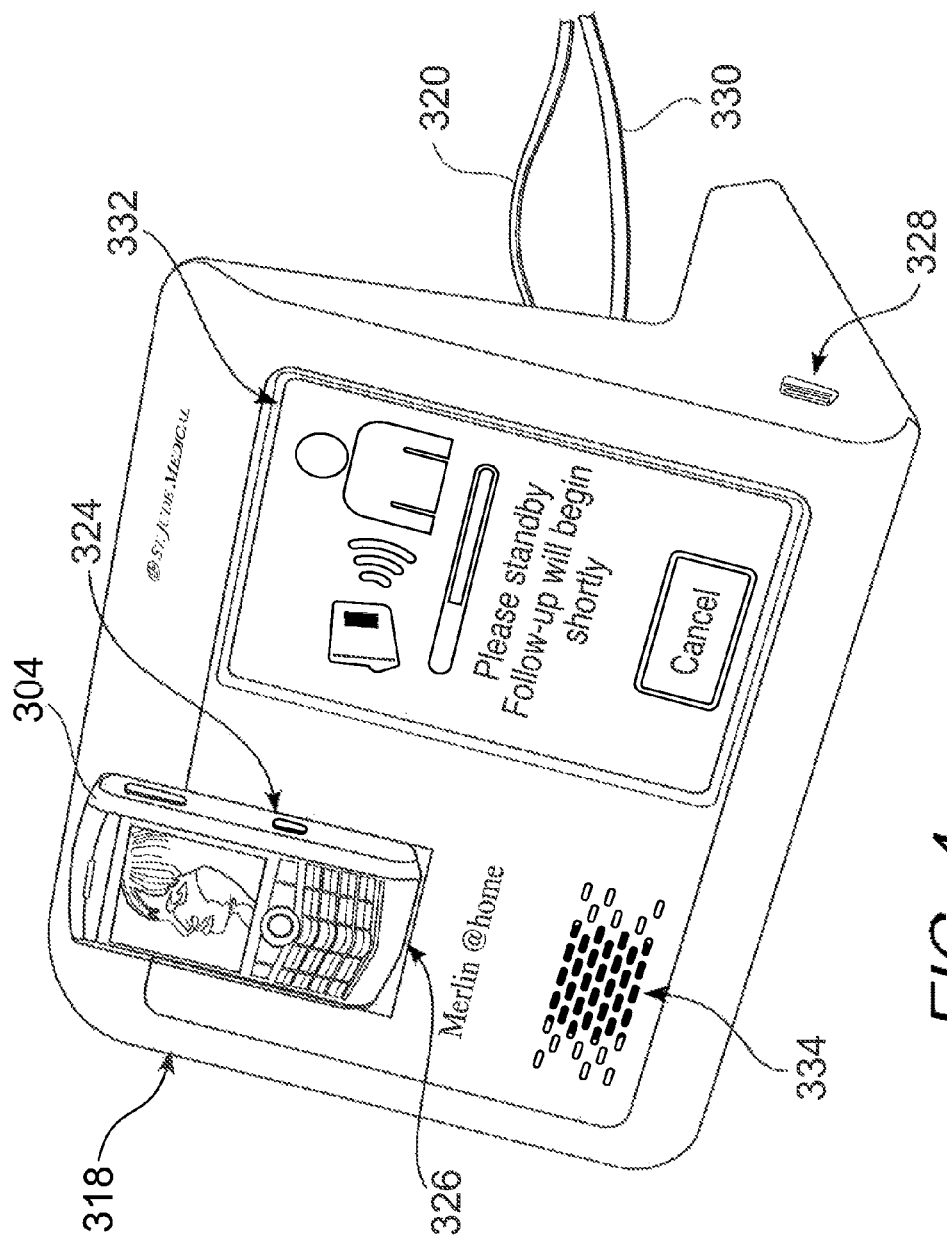
FIG. 4 is a perspective view of an example of a communication device that may from part of the communication system of FIG. 3.

FIG. 4 illustrates an example of a docking station that may comprise the communication device 318 of the communication system 300 of FIG. 3. As shown, the docking station 318 may include a cradle 324 or other suitable structure for receiving the wireless communication device 304. The cradle 324 may include an adapter, plug or other physical interface 326, for example, that is configured to engage an existing port or interface on the wireless communication device 304 such that a communication path may be established when the wireless communication device 304 is properly positioned in the cradle 324.

Alternatively or additionally, the docking station 318 may include a port 328 that is configured to receive a cable (not shown), such as a universal serial bus (USB) or the like, which may be configured to connect to an existing port or interface on the wireless communication device 304 such that a communication path may be established by connecting the wireless communication device 304 to the docking station 318 via the cable.

The communication link 320 may connect the docking station 318, for example, to a telephone network as described above. Further, a power cord 330 may connect the docking station 318 to a power source, such as a power outlet or socket. Thus, the docking station 318 may be conveniently installed in any suitably wired building. As described further below, because the docking station 318 is connected to a power source, the docking station 318 may not only be powered for all of its functions, but may also provide power to the wireless communication device 304 while disposed in the cradle 324 or connected to the docking station 318 via the cable (not shown). This may also conveniently charge a battery of the wireless communication device 304 while connected to the docking station 318.

The docking station 318 may also include a user interface 332, such as a touch screen. The user interface 332 may allow the patient to input data directly into the docking station 318. This may be facilitated by interactive software implemented in the docking station 318. In addition to a display screen, the user interface 332 may include a speaker and/or microphone 334. Thus, both visual and audio output may be provided to the user. Further, in view of the advancements in voice recognition software, it should be appreciated that the speaker and/or microphone 334 may facilitate "hands-free" entering of data by the user into the docking station 318.

The docking station 318 may be configured to automatically download data from the wireless communication device 304 upon being placed in the cradle 324 or connected to the port 328. For example, the docking station 318 may sense when the wireless communication device 304 is connected and initiate a query to the wireless communication device 304 to retrieve data from the implantable cardiac device 100 that is stored in the wireless communication device 304, as described further below. Data may similarly be retrieved from other implanted sensors, either with or without such connection, and may be downloaded to the docking station 318.

Figure 5:
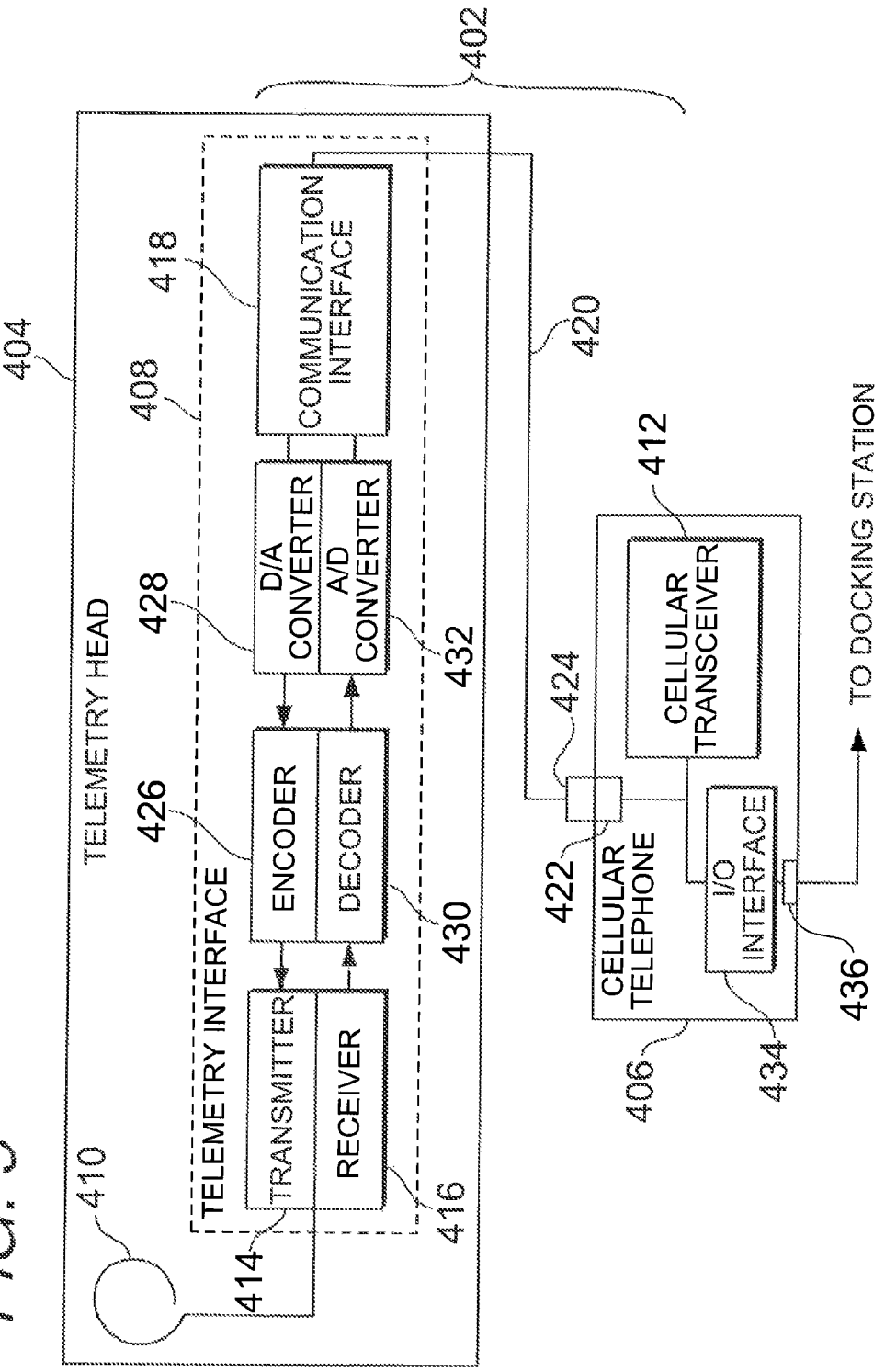
FIG. 5 is a simplified block diagram illustrating a telemetry head, a wireless communication device and a docking station as one embodiment of a communication system.

FIG. 5 illustrates in more detail one embodiment of a communication link 402 between a telemetry head 404 and a cellular telephone 406. The communication link 402 may include a telemetry interface 408 that converts signals received from an antenna 410 in the telemetry head 404 to signals compatible with the cellular telephone 406 and vice versa. For example, the antenna 410 may transmit and receive RF signals. Conversely, a host-side interface of a cellular transceiver 412 in the cellular telephone 406 may send and receive digital data. Accordingly, in some embodiments the telemetry interface 408 may include a transceiver with a transmitter 414 that provides RF signals to the antenna 410 and a receiver 416 that receives RF signals from the antenna 410. In addition, the telemetry interface 408 may include a communication interface 418 that supports an appropriate data format for communicating with the cellular transceiver 412 and/or other components of the cellular telephone 406.

An implanted device (not shown in FIG. 5) may support one or more of a variety of telemetry communication protocols. These protocols may use different encoding schemes and transmission rates. For example, an encoding scheme may involve phase shift modulation, pulse position modulation, digital encoding, etc. Accordingly, the telemetry interface 408 may be configured to support the protocol(s) necessary for communicating with a given implantable cardiac device.

With respect to the transmit path of the telemetry interface 408, the cellular transceiver 412 may send data to the telemetry interface 408 via a communication bus 420. For example, the cellular telephone may support a bus such as the universal serial bus (USB).

In some embodiments the cellular telephone 406 may include a connector (or a receptacle, etc.) 422 that enables an external device to connect to the bus via a complimentary connector (or a receptacle, etc.) 424. In this case, the telemetry head 404 may include a cable with a corresponding connector.

The telemetry interface 408 may include a communication interface 418 such as a bus interface that supports appropriate data formatting and/or protocol conversion to communicate with the cellular telephone 412 over the bus 420. Accordingly, the communication interface 418 may extract raw data from the signals received over the bus 420 and may provide resulting data to an encoder 426. As discussed above, the encoder 426 may provide appropriate encoding for transmitting signals to the implantable cardiac device. At some point in this process, the data may be converted from digital signals to analog signals (e.g., by D/A converter 428). The encoded signals may be provided to the transmitter 414. The transmitter 414 may amplify and filter the signals. In addition, the transmitter 414 may upconvert the signals to an appropriate frequency and/or data rate.

The telemetry interface 408 may include a power supply circuit (not shown) that provides power for the components of the telemetry interface 408. In some embodiments the power supply circuit connects to an appropriate lead or leads on the bus 420 (e.g., a USB bus) to obtain power for the telemetry interface 408 from the cellular telephone 406. In some embodiments the power supply circuit may include a battery.

With respect to the receive path of the telemetry interface 408, signals from the antenna 410 may be provided to the receiver 416. The receiver 416 may amplify and filter the received signals. In addition, the receiver 416 may downconvert the received signals to baseband or intermediate frequency signals. A decoder 430 may decode the received signals as appropriate or desired and may provide the resulting signals to the communication interface 418 which formats the data as appropriate or desired for transmission over the bus 420. At some point in this process, the data may be converted from analog signals to digital signals (e.g., by A/D converter 432).

Data received by the cellular telephone 406 may be sent to the communication device or docking station as described above. For example, the cellular telephone 406 may include an input/output interface 434 that is configured to send and receive data via a connector (or a receptacle, etc.) 436 that enables the cellular telephone 406 to connect to the communication device or docking station (not shown).

It should be understood that the telemetry head 404, the cellular telephone 406 and the communication device or docking station may not always be connected for communication therebetween. For example, the telemetry head 404 may only be connected to the cellular telephone 406 when monitoring of the implantable cardiac device or downloading data therefrom is desired. However, in embodiments in which the telemetry head is incorporated into the wireless communication device, the communication between the wireless communication device and the implantable cardiac device may be enabled and disabled as appropriate or desired. Further, communications between the cellular telephone 406 and the docking station may be wireless. In such cases, it may be advantageous to include an antenna amplifier in the docking station to facilitate such wireless communications (e.g., via RF) by increasing the range. In general, the docking station may improve the range of wireless telemetry by having the docking station provide an effectively larger antenna and/or providing more power.

Also, the cellular telephone 406 may only be connected to the communication device or docking station when downloading data from or uploading of data to the cellular telephone 406 is desired. For example, the cellular telephone 406 may be configured to obtain data from the implantable cardiac device continuously or periodically, as appropriate or desired. The patient may periodically dock or otherwise connect the cellular telephone 406 to the communication device or docking station, for example, daily, to download the obtained data from the cellular telephone 406 to the communication device or docking station. As noted above, this may be conveniently incorporated into the patient's lifestyle, for example, allowing the patient to download data and charge the cellular telephone 406 at the end of the day or overnight.

The telemetry interface 408 described with respect to FIG. 5 may be implemented anywhere along the communication link 402. It should be appreciated that configurations other than those specifically described herein may be utilized. For example, although not shown in a separate figure, it should be understood that the cellular telephone may include any or all of the components of the telemetry head and/or the telemetry interface to be capable of communicating directly with a given implantable cardiac device. Further, one or more components of a telemetry interface may be incorporated into one or more of the telemetry head, a cable, a connector, an accessory for a cellular telephone or some other apparatus. The system may then include appropriate connectivity (e.g., wired-based or wireless-based components) between the system components.

Figure 6:
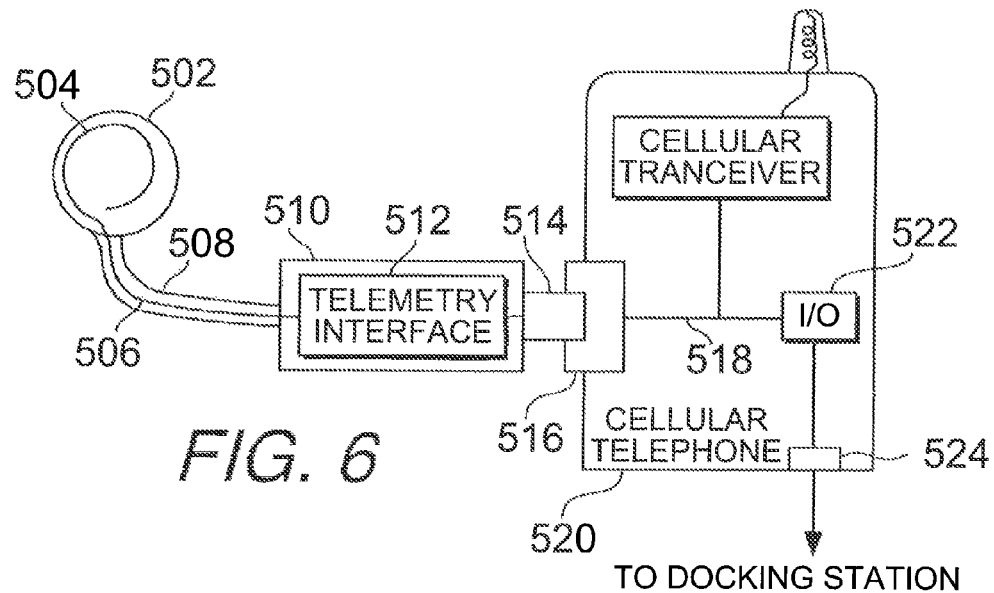
FIG. 6 is a simplified block diagram of a telemetry head and a cellular telephone as part of one embodiment of a communication system.

In FIG. 6 another example of a telemetry head 502 may include an antenna 504 that is connected to one or more leads 506 in a cable 508. A housing 510 attached to the cable 508 may house a telemetry interface 512. A connector 514 may be attached to the end of the cable 508. The housing 510 may also be attached at the end of the cable 508. In this case, the connector 514 may be connected to (e.g., mounted on or in) or integrated with the housing 510. In some embodiments, at least a portion of the connector 514 may be incorporated into the housing 510.

As discussed above, the connector 514 may be configured to mate with a compatible connector 516 (e.g., a USB connector or the like) on a cellular telephone 518. In this way, data received via the antenna 504 may be provided to a bus 518 in the cellular telephone 520 and vice versa. Further, the cellular telephone 520 may include an input/output interface 522 that is configured to send and receive data via a connector (or a receptacle, etc.) 524 that enables the cellular telephone 520 to connect to the communication device or docking station (not shown).

Figure 7:
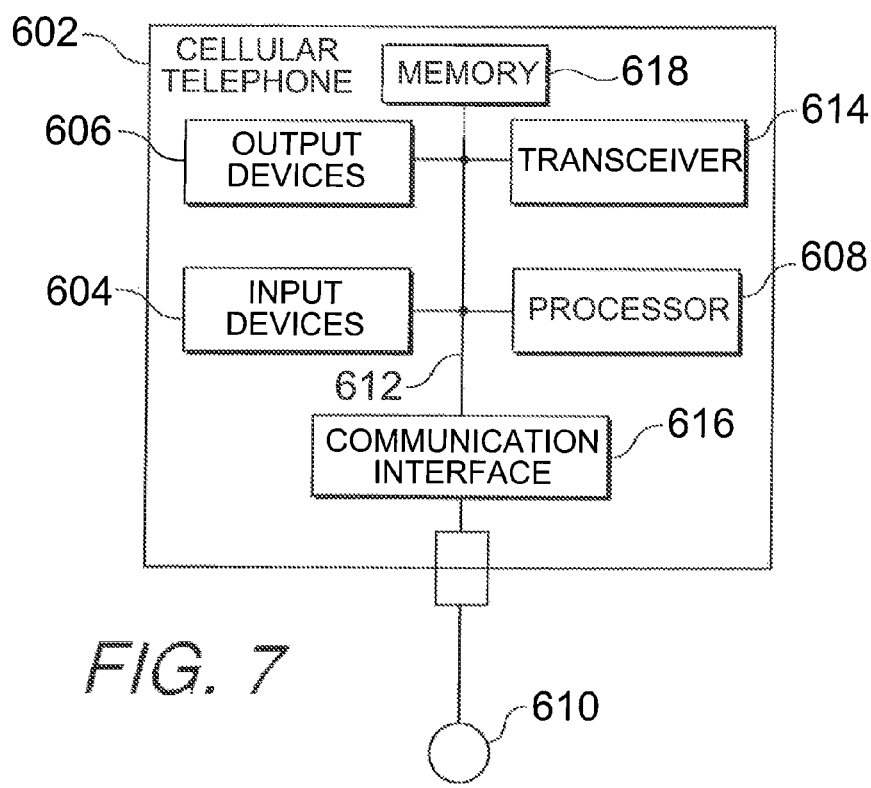
FIG. 7 is a simplified block diagram of a cellular telephone as part of one embodiment of a communication system.

In some embodiments, the operation of the telemetry head and/or the uploading and downloading of data may be controlled via the cellular telephone. Referring to FIG. 7, a cellular telephone 602 may include various input devices (e.g., a key pad, display soft keys, a microphone, etc.) 604 and output devices (e.g., a display, a speaker, etc.) 606. A processor 608 may be configured (e.g., via software) to control the operation of these components and control the flow of data to and from a telemetry head 610. For example, the processor 608 may be configured to establish a connection with a remote system (not shown in FIG. 7) to initiate uploading data from or downloading data to the implantable cardiac device (not shown in FIG. 7). The processor 608 also may be configured to receive a connection request from the remote device to initiate an upload or download. To this end, the processor 608 or some other component may control data flow over an internal bus 612 between a cellular transceiver component 614 and a communication interface (e.g., a bus interface) 616 in the cellular telephone 602.

Alternatively, the processor 608 may be configured to initiate uploading data from or downloading data to the implantable cardiac device independently. In such case, the communication interface 616 may establish a connection with a remote system when the processor 608 directs downloading of data to the remote system.

The cellular telephone 602 may include a memory 618 or other storage device for temporarily storing the data from the implantable cardiac device prior to downloading to the remote system or the communication device/docking station. The memory may allow the cellular telephone 602 to continuously or periodically obtain data from the implantable cardiac device, for example, when a connection to a cellular network or connection to the communication device/docking station is not possible. Thus, a patient may have the cellular telephone obtain data from the implantable cardiac device, as appropriate or desired, and send the obtained data to the remote system or the communication device/docking station when convenient or accessible.

Figure 8:
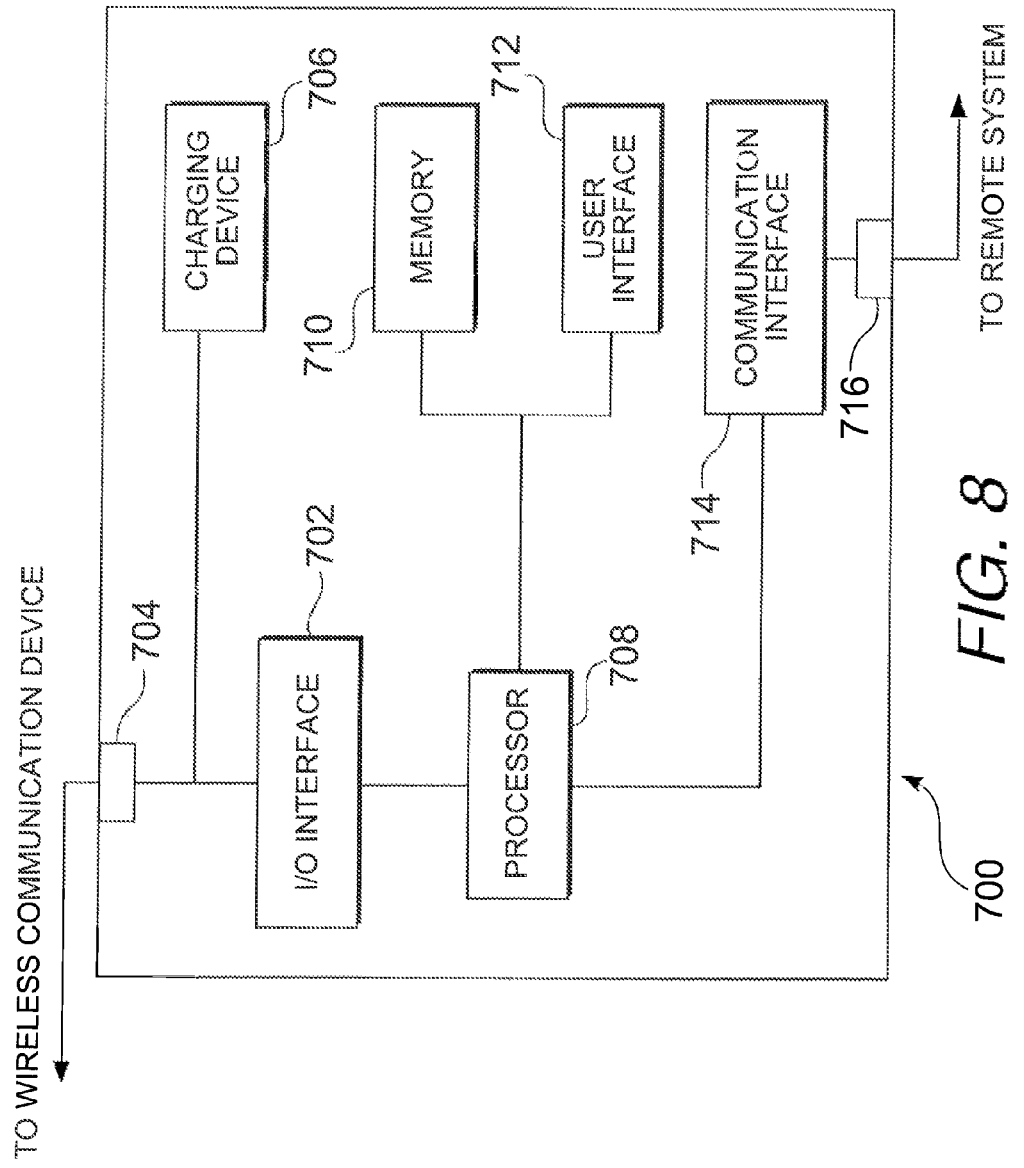
FIG. 8 is a simplified block diagram of an example of a docking station as one embodiment of a communication device.

FIG. 8 illustrates a simplified block diagram of an embodiment of a communication device or docking station 700. The docking station 700 may include an input/output interface 702 that is configured to send and receive data from a wireless communication device (not shown), for example, via a connector 704. In the embodiment shown, the docking station 700 may also include a charging device 706 that allows the docking station 700 to supply power to and/or charge the wireless communication device while connected to the connector 704. As discussed above, the communications between the docking station 700 and the wireless communication device may be wireless, and the docking station 700 may include an antenna amplifier (not shown) to facilitate such wireless communications.

The docking station 700 may include a processor 708 that is configured to control operation of the various components of the docking station 700. Further, the processor 708 may be configured to analyze data of the implantable cardiac device received from the wireless communication device. Thus, the docking station 700 may be capable of data analysis that allows the patient and/or the clinician to be provided with a result of the analysis without requiring further communication to a remote system for analysis. Further, the local analysis may allow the docking station 700 to reprogram or adjust operating parameters of the implantable cardiac device by sending data to the implantable cardiac device via the wireless communication device, without requiring further communication to the remote system for analysis. This may save time by avoiding delays in analysis and/or communication, which may be critical for the patient.

The docking station 700 may include a memory 710 for temporarily storing data received from the wireless communication device. The memory 710 may also facilitate operations of the processor 708 in a manner known in the art.

As discussed above with respect to FIG. 4, the docking station 700 may include a user interface 712 that avows a user to input data in addition to the data received from the wireless communication device. The processor 708 may be configured to use the data input via the user interface 712 to analyze the data received from the wireless communication device and/or otherwise incorporate the data input via the user interface 712 with the analysis and/or the raw data received from the wireless communication device, for example, for transmission to a remote device (not shown).

The processor 708 may use a communication interface 714 to communicate with the remote system via a suitable connector 716. The communication interface 714 may comprise a land-line modem and/or a wireless (e.g., cellular) interface. As discussed above, the connector 716 may be a telephone jack for connecting the docking station 700 to a telephone network. Communication to the remote system may provide information to the clinician or other appropriate service providers, as well as to facilities that may provide further analysis of the data. Communication to the remote system may thus facilitate a more complete evaluation of the patient's condition and/or the implantable device's operation, which may be useful for continued care of the patient, as well as for medical studies in general.

Figure 9:
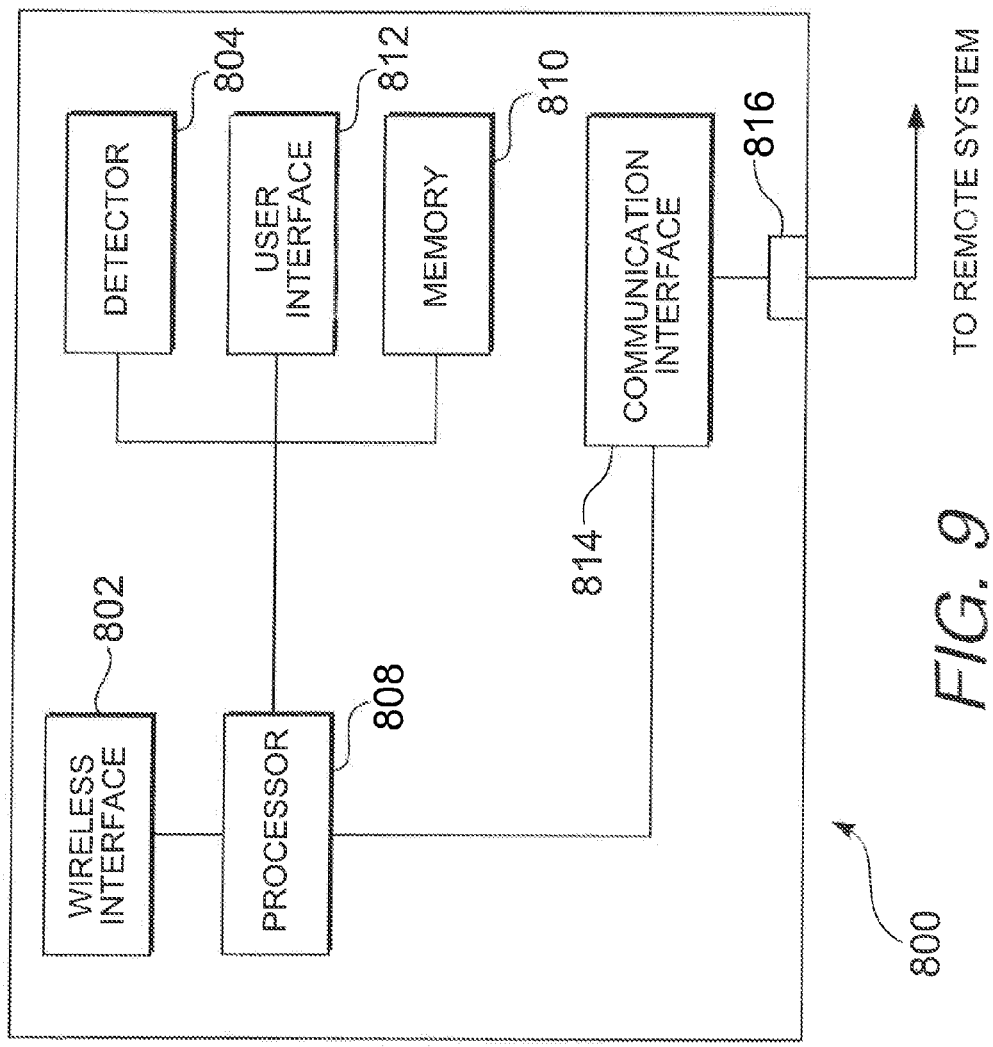
FIG. 9 is a simplified block diagram of another example of a docking station as one embodiment of a communication device.

FIG. 9 illustrates a simplified block diagram of another embodiment of a communication device or docking station 800. Similar to the docking station 700 described with respect to FIG. 8, the docking station 800 may include a processor 808, a memory 810, a user interface 812, a communication interface 814 and a connector 816, which may provide similar functions. Instead of the input/output interface 702 and connector 704, however, the docking station 800 may include a wireless interface 802 that is configured to send and receive data from a wireless communication device (not shown).

In the embodiment shown, the docking station 800 may also include detector 804 that is configured to sense when the wireless communication device is within range of the docking station 800 for wireless communication. For example, rather than physically connecting the wireless communication device to the docking station 800, the docking station 800 may initiate or establish communication with the wireless communication device upon detection thereof. This may reduce or even eliminate a need for the patient to remember to dock or connect the wireless communication device to the docking station 800 to download data. This may also provide more frequent downloading of data, which may enhance patient care, for example, by providing more frequent analysis of data and/or adjustments of the implantable cardiac device.

In any of the embodiments of the communication device/docking station, the communication device/docking station may be configured to provide all or nearly all of the functionality required for obtaining data from and providing data to the implantable cardiac device, for example, such that a conventional wireless communication device may be used. For example, the communication device/docking station may include a suitable encoder, decoder and/or converters to facilitate communications with the wireless communication device, the implantable cardiac device and the remote system.

Alternatively or additionally, the communication device/docking station may be configured to provide a conventional wireless communication device with software that adds new features or functions to the wireless communication device. Thus, the communication device/docking station may be configured to provide updates to the wireless communication device, in addition to providing updates to the implantable cardiac device.

Figure 10:
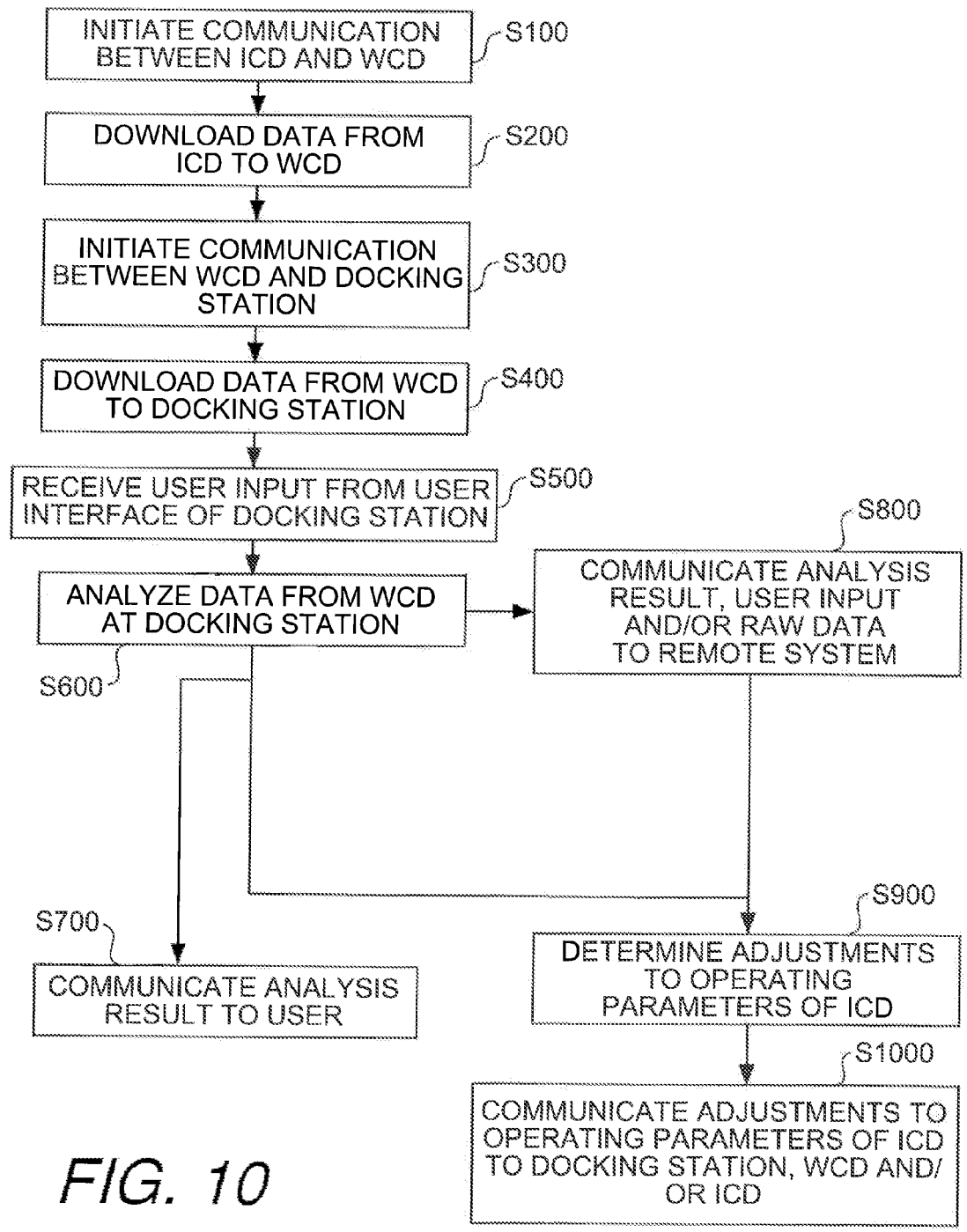
FIG. 10 is a flow chart illustrating an example of a communication method that may be implemented by a communication device or system with an implantable cardiac device.

Referring now to FIG. 10, a flow chart illustrating an embodiment of a communication method that may be implemented by a communication device or system, such as described above, with an implantable cardiac device is shown. It should be understood that the various steps shown may be optional and that other steps may be added as desired, and that the order of steps shown may be rearranged as desired. The flow chart is intended to illustrate one non-limiting example for the sake of understanding a general approach to communicating with an implantable cardiac device, and is not intended to encompass all of the possibilities contemplated herein and/or permutations that may be appropriate for a given application.

Beginning in step S100, a communication between the implantable cardiac device and the wireless communication device may be initiated. It should be understood that the communication may be via a separate telemetry head or via suitable circuitry in the wireless communication device, as described herein.

The communication may be initiated at the direction of the implantable cardiac device or the wireless communication device. For example, the implantable cardiac device may continuously or periodically "search" for a compatible wireless communication device or a specified wireless communication device with which to communicate, or may continuously or periodically transmit data so that communication may be established by receipt of the transmission by the wireless communication device.

Alternatively, the wireless communication device may continuously or periodically "search" for the implantable cardiac device. Once located within range for wireless communication, the implantable cardiac device may automatically transmit data or otherwise initiate the communication, or the wireless communication device may initiate the communication, for example, by querying the implantable cardiac device for data to initiate the communication.

As yet another alternative, a user, such as the patient, may initiate the communication between the implantable cardiac device and the wireless communication device, for example, using the wireless communication device or the telemetry head, when provided.

In any case, once the communication is established, data from the implantable cardiac device is downloaded to the wireless communication device in step S200. The downloading of data may be via any suitable type of transmission, such as RF.

In step S300, a communication between the wireless communication device and the docking station (communication device) may be initiated. As described above, the communication may be initiated at the direction of the docking station. For example, the docking station may continuously or periodically "search" for a compatible wireless communication device or a specified wireless communication device with which to communicate. Although not described above, it should be understood that the wireless communication device may be configured to continuously or periodically "search" for a compatible docking station or a specified docking station with which to communicate. Once located within range for wireless communication, the wireless communication device may automatically transmit data or otherwise initiate the communication, or the docking station may initiate the communication, for example, by querying the wireless communication device for data.

Alternatively, the wireless communication device and/or the docking station may initiate the communication by connecting the wireless communication device to the docking station, for example, by placing the wireless communication device in the cradle of the docking station. Once connected, the wireless communication device may automatically transmit data or otherwise initiate the communication, or the docking station may initiate the communication, for example, by querying the wireless communication device for data to initiate the communication.

As yet another alternative, a user, such as the patient, may initiate the communication between the implantable cardiac device and the wireless communication device, for example, using the wireless communication device or the docking station, when connected or within apparent wireless range.

In any case, once the communication is established, data from the wireless communication device is downloaded to the docking station in step S400. Again, the downloading of data may be via any suitable type of transmission.

In step S500, the user or patient may input data into the docking station via the user interface of the docking station. The user input data may be, for example, related to any medically relevant information of which the user is aware and that the implantable cardiac device is not configured to provide. For example, the patient may input his general condition, such as fatigued, or other relevant factors, such as exercise or exertion recently performed. If not associated with the implantable cardiac device or the docking station, the patient may input personal data, for example, by entering the data or a code that is associated with his personal and/or medical information. The user may enter, for example, weight, blood pressure, number of pillows required for sleep or answers to specific questions provided from the clinic (for example, downloaded to the docking station) about medications or other factors for tailored patient care. Thus, the user interface may be used to enter additional information that supplements and/or identifies the data from the implantable cardiac device.

The docking station may perform an analysis of the data received from the user interface and/or the wireless communication device in step S600. For example, the docking station may perform an analysis that identifies problems with the patient's health and/or the operation of the implantable cardiac device. In particular, a change in the patient's condition, such as left atrial pressure (LAP), pulmonary embolism (PE), cardiogenic impedence, ischemia, etc., may be detected that may require corrective action other than that which the implantable cardiac device is currently configured to perform. If the patient has other implantable sensors, the data from such sensors may be combined and used as part of the analysis discussed above.

In step S700, the result(s) of the analysis performed by the docking station in step S600 may be communicated to the user. For example, a visual and/or audio communication may be provided to the patient via the user interface of the docking station. Alternatively, a separate contact of the patient can occur, for example, via a SMS (short message service) message via a cell phone, a landline telephone call, or any other suitable communication.

Although not shown, step S700 may include communicating the result(s) of the analysis performed by the docking station in step S600 to the patient's physician, a local ambulance service and/or a local hospital. Thus, it will be appreciated that the communication provided in step S700 may be an "alert" to the patient and/or others trained to deal with a particular condition, for example, indicated by the result(s).

Also, the result(s) of the analysis performed by the docking station in step S600, the information input by the user via the user interface and/or the raw data received by the docking station from the wireless communication device may be communicated to a suitable remote system. The remote system may be configured to provide further analysis of the result(s) and/or the raw data, to collect the result(s) and/or the raw data, to communicate the result(s) and/or the raw data to appropriate parties (e.g., physicians, medical researchers, etc.), and/or to provide any other known or hereafter developed useful service. For example, the docking station may provide the user with an option of obtaining messages and/or specific instructions from the physician when the wireless communication device is docked or otherwise in communication with the docking station. The docking station may be configured to provide software updates to the wireless communication device, for example, to automatically update the wireless communication device with a new version of software when the wireless communication device is docked or otherwise in communication with the docking station.

In step S900, either based on the result(s) of the analysis performed by the docking station in step S600 and/or result(s) of the analysis performed by the remote system in step S800, a determination may be made regarding any adjustments to operating parameters or other programming of the implantable cardiac device in response. For example, the result(s) of the analysis may indicate that a different pacing configuration is appropriate or that a different threshold for corrective action by the implantable cardiac device should be set to improve the health of the patient and/or reduce the patient's risk to adverse cardiac conditions.

If adjustments to the operating parameters or other programming of the implantable cardiac device are determined in step S900, then such adjustments and/or programming may be communicated to the implantable cardiac device. For example, such communication may be made to the wireless communication device via the docking station, for example, when the wireless communication device is connected to the docking station or within range of wireless communication from the docking station. Alternatively, such adjustments and/or programming may be communicated directly to the wireless communication device, for example, from the remote system. Further, when appropriate or desired, the patient may be requested to go to a facility, such as a hospital or physician's office, to have the adjustments and/or programming communicated to the implantable cardiac device.

Although not illustrated in the flow chart of FIG. 10, it should be understood that other functions or operations may be performed by a communication device, communication system or communication method for communicating with an implantable cardiac device. For example, as described above, the docking station may be configured to add software, updates or other features to the wireless communication device (e.g., cell phone) as appropriate or desired.

The docking station may be used to perform offline analyses (i.e., analyses conducted by the docking station without being in communication with the remote system) on raw data collected by the implanted device. While the wireless communication devices, such as cell phones, may be used to collect raw data from the implanted device for forwarding to the docking station or the remote system, such wireless communication devices typically are not capable of performing such offline analyses due to insufficient memory or processing power. The capability of the docking system to provide offline analysis capability allows a determination to be made locally regarding a patient condition (e.g., LAP, PE, cardiac impedance, ischemia detection, etc.) and whether the condition warrants the sending of an alert to the patient locally via the docking station or cell phone or to the patient's physician via the remote system.

While a patient may enter data into, and receive feedback from, the data interfaces (e.g., keypad and screen) of a wireless communication device, such as a cell phone, such data interfaces are small and not overly user friendly for a patient, much less an elderly patient. Advantageously, the data interfaces (e.g., key pad, touch screen, display screen, etc.) of the docking station provide the patient with enlarged and user-friendly data interfaces.

Although communication to the remote system is illustrated as being via the docking station, it should be understood direct wireless communication from the wireless communication device to the remote system may be possible, with communication via the docking station being an alternative or backup method. For example, the wireless communication device (e.g., cell phone) may communicate with the implanted medical device via RF or other communication means to obtain information, which the cell phone communicates to the remote system via a cell network. However, the patient may travel into an area wherein the cell phone is unable to communicate with the remote system (e.g., an area without cell coverage). As the person engages in activities within the area without cell coverage, the cell phone continues to communicate with the implanted medical device and stores the communicated information in a memory of the cell phone. Upon cell coverage becoming available, the cell phone may communicate the stored information to the remote system via the cell network. However, in the event cell coverage does not again become available or the patient simply prefers to analyze the stored information locally, the cell phone may be placed in the docking station and the stored information may be downloaded into the docking station. The docking station may then forward the stored information to the remote system, or the docking station may analyze locally the stored information.

Further, although not specifically illustrated in FIG. 10, it should be understood that data from one or more implanted sensors may be communicated to the wireless communication device, and then communicated to and processed by the docking station. The data analysis may allow the docking station to provide information or control signals to the implanted medical device via the wireless communication device.

A method of communicating information received from an implantable medical device 100 is disclosed herein and discussed with reference to FIGS. 3 and 4. In one embodiment, the method includes wirelessly communicating information from the implanted medical device 100 to a wireless communication device 304, such as a cellular telephone 304. It is determined if wireless communication can be established between the wireless communication device 304 and a remote system 308 at a first point in time. If it is determined that wireless communication can be established between the wireless communication device 304 and the remote system 308 at the first point in time (e.g., because cell coverage is available), the information is wirelessly communicated to the remote system 308. However, if it is determined that wireless communication cannot be established between the wireless communication device 304 and the remote system 308 at the first point in time (e.g., because cell coverage is not available), the information is stored in a memory 618 (see FIG. 7) of the wireless communication device 304 until the information can be communicated to which ever of the remote system 308 or a docking station 318 to be first placed in communication with the wireless communication device 304 at a second point in time subsequent to the first point in time.

In one embodiment, if the information is communicated to the docking station 318, the docking station 318 is employed to analyze the information. Further, in such an embodiment, the information may be forwarded from the docking station 318 to the remote system 308.

Another method of communicating information received from an implantable medical device 100 is disclosed herein and discussed with reference to FIGS. 3 and 4. In one embodiment, the method includes wirelessly communicating information from the implanted medical device 100 to a wireless communication device 304, such as a cellular telephone 304. It is determined if a local analysis of the information is preferred over analysis via a remote system 308. If it is determined that local analysis is preferred over analysis via the remote system 308, the information is stored in a memory 618 (see FIG. 7) of the wireless communication device 304 and delivered to a docking station 318. If it is determined that analysis via the remote system 308 is preferred over local analysis, the information is delivered to the remote system 308.

In one embodiment, if the information is communicated to the docking station 318, the docking station 318 is employed to analyze the information. In such an embodiment, the docking station 318 may also forward the information to the remote system 308. In one embodiment, if the information is communicated to the remote system 308, the remote system is employed to analyze the information.

It should be appreciated from the above that the various structures and functions described herein may be incorporated into a variety of apparatuses and implemented in a variety of ways. Different embodiments of the device may include a variety of hardware and software processing components. In some embodiments, hardware components such as processors, controllers, state machines and/or logic may be used to implement the described components or circuits. In some embodiments, code such as software or firmware executing on one or more processing devices may be used to implement one or more of the described operations or components.

The components and functions described herein may be connected and/or coupled in many different ways. The manner in which this is done may depend, in part, on whether and how the components are separated from the other components. In some embodiments some of the connections and/or couplings represented by the lead lines in the drawings may be in an integrated circuit, on a circuit board or implemented as discrete wires or in other ways.

The signals discussed herein may take several forms. For example, in some embodiments a signal may comprise electrical signals transmitted over a wire, light pulses transmitted through an optical medium such as an optical fiber or air, or RF waves transmitted through a medium such as air, etc. In addition, a plurality of signals may be collectively referred to as a signal herein. The signals discussed above also may take the form of data. For example, in some embodiments an application program may send a signal to another application program. Such a signal may be stored in a data memory.

While certain exemplary embodiments have been described above in detail and shown in the accompanying drawings, it is to be understood that such embodiments are merely illustrative of and not restrictive of the broad invention. In particular, it should be recognized that the teachings provided herein apply to a wide variety of systems and processes. It will thus be recognized that various modifications may be made to the illustrated and other embodiments described herein, without departing from the broad inventive scope thereof. In view of the above it will be understood that the invention is not limited to the particular embodiments or arrangements disclosed, but is rather intended to cover any changes, adaptations or modifications which are within the scope and spirit of the disclosure provided herein.

What is claimed is:

1. A non-implantable communication device for use with an implantable medical device,
    a wireless communication device that wirelessly communicates with the implantable medical device, and
    a remote system with which the wireless communication device can wirelessly communicate when wireless communications can be established therebetween,
    the non-implantable communication device comprising:
    an input/output interface configured to communicate with the wireless communication device that wirelessly communicates with the implantable medical device, to thereby receive data associated with the implantable medical device from the wireless communication device;
    a communication interface configured to communicate with the remote system; and
    a processor configured to perform a local analysis of data received from the wireless communication device via the input/output interface and associated with the implantable medical device, wherein the local analysis is performed without the remote system; and
    wherein the processor is also configured to use the communication interface to communicate with the remote system to enable a remote analysis of data received from the wireless communication device via the input/output interface and associated with the implantable medical device; and
    wherein the communication interface enables wired communication between the wireless communication device and the remote system when wireless communications cannot be established therebetween, thereby providing at least one of a backup or redundant way for sending, to the remote system, data received from the wireless communication device via the input/output interface and associated with the implantable medical device.

2. The non-implantable communication device of claim 1 wherein the local analysis that the processor is configured to perform identifies at least one of left atrial pressure, pulmonary embolism, cardiogenic impedance or cardiac ischemia.

3. The non-implantable communication device of claim 1 wherein the processor is further configured to provide a communication to at least one of the wireless communication device, the remote system or a user of the non-implantable communication device based on a result of the local analysis.

4. The non-implantable communication device of claim 1 wherein the processor is further configured to provide an adjustment of at least one operating parameter to the implantable medical device based on a result of the local analysis.

5. The non-implantable communication device of claim 1 wherein the processor is configured to send to the remote system at least one of the data received from the wireless communication device, an analysis of the data received from the wireless communication device, or a result of the local analysis via the communication interface non-wirelessly.

6. The non-implantable communication device of claim 1 wherein the processor is configured to send data received from the remote system via the communication interface to the wireless communication device via the input/output interface.

7. The non-implantable communication device of claim 6, wherein the data received from the remote system and sent to the wireless communication device comprises an adjustment of at least one operating parameter of the implantable medical device.

8. The non-implantable communication device of claim 1, further comprising:
 a user interface configured to receive data input by a user;
 wherein the processor is also configured to communicate data received from the wireless communication device via the input/output interface and data received from the user interface to the remote system.

9. The non-implantable communication device of claim 8, wherein the user interface comprises a touch screen.

10. The non-implantable communication device of claim 8, wherein the user interface is configured to provide an output to the user based on a result of the local analysis.

11. The non-implantable communication device of claim 1, further comprising:
 a connector configured to be connected with a port or interface of the wireless communication device and thereby provide a communication path between the input/output interface and the wireless communication device; and
 a charging component configured to supply power to and/or charge the wireless communication device while the wireless communication device is connected with the connector.

12. The non-implantable communication device of claim 11, wherein:
 the wireless communication device that wirelessly communicates with the implantable medical device comprises a cellular telephone;
 the non-implantable communication device comprises a docking station for the cellular telephone; and
 the charging component is configured to supply power to and/or charge the cellular telephone when the cellular telephone is docked in the docking station and the connector is connected with the cellular telephone.

13. The non-implantable communication device of claim 12, wherein:
 the cellular telephone can use a cellular network to communicate with the remote system when cellular coverage is available; and
 the communication interface enables wired communication between the cellular telephone and the remote system when cellular coverage for the cellular telephone is unavailable.

14. A non-implantable communication device for use with an implantable medical device,
a wireless communication device that wirelessly communicates with the implantable medical device, and
a remote system,
the non-implantable communication device comprising:
an input/output interface configured to communicate with the wireless communication device that wirelessly communicates with the implantable medical device, to thereby receive data associated with the implantable medical device from the wireless communication device;
a communication interface configured to communicate with the remote system; and
a processor configured to
 determine, for data that may be analyzed both locally and remotely, if a local analysis is preferred over a remote analysis;
 perform a local analysis of data received from the wireless communication device via the input/output interface, if the processor determines that local analysis is preferred over remote analysis; and
 use the communication interface to transfer data to the remote system, to enable a remote analysis of data received from the wireless communication device via the input/output interface, if the processor determines that remote analysis is preferred over local analysis.

* * * * *